United States Patent [19]
Bundy et al.

[11] Patent Number: 4,851,586
[45] Date of Patent: Jul. 25, 1989

[54] 1,4-NAPHTHALENEDIOL AND 1,4-HYDROQUINONE DERIVATIVES

[75] Inventors: Gordon L. Bundy; Chiu-Hong Lin, both of Portage, Mich.

[73] Assignee: The Upjohn Company, Kalamazoo, Mich.

[21] Appl. No.: 65,534

[22] PCT Filed: Sep. 5, 1986

[86] PCT No.: PCT/US86/01852
§ 371 Date: May 18, 1987
§ 102(e) Date: May 18, 1987

[51] Int. Cl.$^4$ .......................................... C07C 43/215
[52] U.S. Cl. .................................. 568/633; 549/416
[58] Field of Search ........................................ 568/633

[56] References Cited

U.S. PATENT DOCUMENTS

| | | | |
|---|---|---|---|
| 4,102,902 | 7/1978 | Archer et al. | 260/345 |
| 4,388,312 | 6/1983 | Terao et al. | 424/244 |
| 4,407,757 | 10/1983 | Morimoto et al. | 260/413 |

FOREIGN PATENT DOCUMENTS

| | | |
|---|---|---|
| 92136A | 4/1982 | European Pat. Off. . |
| 124379A | 5/1983 | European Pat. Off. . |
| 124379A | 5/1983 | European Pat. Off. . |
| 103361A | 6/1983 | European Pat. Off. . |
| 0106341 | 10/1983 | European Pat. Off. . |
| 38160B | 9/1984 | European Pat. Off. . |
| 3311922A | 4/1982 | Fed. Rep. of Germany . |
| 56-140943 | 4/1980 | Japan . |
| 57-120519 | 1/1981 | Japan . |
| 57-128624 | 2/1981 | Japan . |
| 58083698 | 11/1981 | Japan . |
| 58-174342A | 4/1982 | Japan . |
| 58-174343A | 4/1982 | Japan . |
| 59010541A | 7/1982 | Japan . |
| 60075442A | 9/1983 | Japan . |

OTHER PUBLICATIONS

Snyder et al., JACS, 96, 8046 (1974).
M. Shiraishi et al., Synthesis of Quinone Derivatives having Ethylenic and Acetylenic Bonds: Specific Inhibitors of the Formation of Leukotrienes and 5-Hydroxyicosa-6,8,11,14-tetraenoic Acid (5-HETE), J. Chem. soc. Perkin Trans. I, 1591-1599 (1983).
T. Yoshimoto et al., 2,3,5-Trimethyl-6-(12-Hydroxy-5,10-Dodecadiynyl)1,4-Benzoquinone (AA861), A Selective Inhibitor of the 5-Lipoxygenase Reaction and the Biosynthesis of Slow-Reacting Substance of Anaphylaxis, Biochim. Biophys. Acta., 713:470-473 (1982).
Y. Ashida et al., Pharmacological Profile of AA-861, A 5-Lipoxygenase Inhibitor, Prostaglandins 26(No. 6):955-972 (1983).
K. Ohuchi et al., Inhibition by AA861 of Prostaglandin E$_2$ Production by Activated Peritoneal Macrophages of Rat, Prostaglandins, Leukotrienes and Medicine, 12:175-77 (1983).
M. Shiraishi et al., Studies on the Synthesis of 5-Lipoxygenase Inhibitors, J. Pharmacobiodyn, 7:S-95 (1984), Derwent Abstract 84-44729.
S. Yamamoto et al., Arachidonate 5-lipoxygenase and its new inhibitors, J. Allergy Clin. Immunol., 74:349-352 (1984).

*Primary Examiner*—Nicky Chan
*Attorney, Agent, or Firm*—Martha Cox

[57] ABSTRACT

Novel 1,4-naphthalenediol and 1,4-hydroquinone derivatives of formulas I, II, III and IV and their therapeutic uses as 5-lipoxygenase inhibitors, leukotriene inhibitors, antiinflammatory and/or inhibitors of mucus secretion agents are described. Also provided are novel intermediates useful for the preparation of said derivatives.

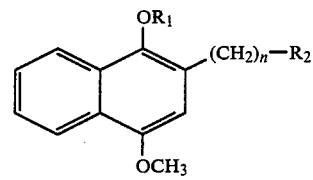

I

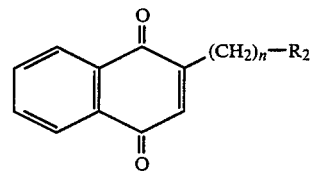

II

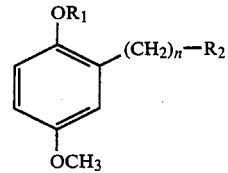

III

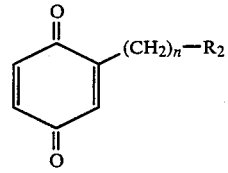

IV

3 Claims, No Drawings

1,4-NAPHTHALENEDIOL AND 1,4-HYDROQUINONE DERIVATIVES

BACKGROUND OF THE INVENTION

The novel 1,4-naphthalenediol and 1,4-hydroquinone compounds of the present invention are 5-lipoxygenase and leukotriene inhibitors and as such are useful for treating diseases that result in bronchial constriction such as bronchial asthma, bronchitis, brochiectasis, pneumonia and emphysema. Some of the compounds of this invention also exhibit varying degrees of thromboxane $A_2$ synthetase inhibiting activity and/or cyclooxygenase inhibiting activity as well. For many of the intended applications, such as asthma, bronchitis, brochiectasis, pneumonia and emphysema, the combination of the three inhibiting effects may be desirable for some of the intended applications.

The leukotrienes are a class of unsaturated fatty acid compounds which are derived from arachidonic acid by the action of lipoxygenase. See, e.g., Samuelsson, Trends in Pharmacological Sciences, 5: 227 (1980); and Samuelsson, et al., Annu. Rev. Biochem. 47: 997-1029 (1978). For a discussion of leukotriene nomenclature, see Samuelsson, et al., Prostaglandins, 19: 645 (1980).

The leukotrienes have been found to be potent constrictors of human bronchi. That is, certain leukotrienes are mediators of the action of slow-reacting substance of anaphylaxis (SRS-A). See, e.g., Dhalen, Nature, 288: 484 (1980). These compounds are therefore important mediators of bronchoconstriction in humans.

The role of leukotrienes as agonists in immediate hypersensitivity and other pathological conditions had led to research into leukotriene antagonists and inhibitors of leukotriene biosynthesis. See, e.g., Corey, et al., Tet. Lett. 21: 4243 (1980).

Leukotrienes, particularly leukotriene $C_4$ ($LTC_4$) and leukotriene $D_4$ ($LTD_4$) have been shown to be potent mucus secretagogues. Mucus secreted from submucosal glands and surfaces at the epithelial cells combines with water to form part of the respiratory tract secretions. In healthy states mucus secretion in the respiratory tract is about 50 to 150 ml per day in man. The excessive production of mucus, however, is an important feature of many pulmonary diseases. For example, in chronic bronchitis the flow of mucus increases up to fourfold. The lack of the ability of the patient to deal with this hyper-production leads to pathological conditions of the airways such as chronic bronchitis, asthma, and cystic fibrosis where there is a defect in consistency or clearance of the mucus. Therefore it is medically desirable to regulate the hypersecretion of mucus (J. G. Widdicobe, Brit. Med. Bull. 34, 57–31 (1978)). Historically attempts have been made to treat the symptoms without regulation of the root cause. For example, mucolytics, acetylcysteine containing solutions, as well as iodides have been used. Also, antibiotics are used to treat infections in cystic fibrosis because no known drug can regulate the consistency of the mucus in this disease condition. Both $LTC_4$ and $LTD_4$ increase the release of mucus from human airways in vitro, Z. Maron, et al., Am. Rev. Respir. Dis. 126, 449-451 (1982); S. J. Coles, et al., Prostaglandins 25, 155-170 (1983), and from canine tracheas in vivo, H. G. Johnson, et al., Int. J. Immunopharmacol. 5, 178 (1983); H. G. Johnson, et al., Prostaglandins 25, 237-243 (1983). Arachidonic acid, metabolic products or arachidonic acid, monohydroxyeicosatetraenoic acid, and prostaglandins also release mucus from human airways, Z. Maron, et al., J. Clin. Invest. 67, 1695-1702 (1981). $LTC_4$ was effective in stimulating mucus release in vivo in the cat but not in vitro in cat trachea tissue, A. C. Peatfield, et al., Br. J. Pharmac. 77, 391-393 (1982). J. H. Shelhamer, et al., Chest. 81, 36s (1982) summarizes the nature of evidence available suggesting that lipoxygenase products generated by the airways in vitro might be responsible for the augmented mucus release.

O. Cromwell, et al., The Lancet, July 25, 1981, pp. 164–165, identified $LTB_4$ and $LTD_4$ in the sputum of cystic fibrosis patients and speculated, therefore, that inhibitors of the lipoxygenase pathway might be capable of reversing the airway obstruction in such patients.

T. Ahmed, et al., Am. Rev. Respir. Dis. 124, 110-114 (1981) demonstrated FPL 55712, an $LTC_4$ antagonist when given prior to antigen challenge was effective in reversing the tracheal mucus velocity in patients with a history of bronchial asthma but concluded that the clinical significance of FPL 55712 remains to be demonstrated.

In mammalian metabolism, arachidonic acid is transformed to 12-L-hydroperoxy-5,8,10,14-eicosatetraenoic acid by the action of 12-lipoxy-genase. See, Hamberg, et al., Proc. Nat. Acad. Sci. 71: 3400– 3404 (1974). Similarly, 5-lipoxygenase transforms arachidonic acid into 5-S-hydroperoxy-6,8,11,14-eicosatetraenoic acid. Thus, an agent which inhibits the action of lipoxygenase would be useful in treating or preventing untoward conditions associated with lipoxygenase products.

Therefore, compounds which inhibit the action of lipoxygenase are useful in the treatment of inflammatory conditions where it is desirable to prevent migration of polymorphonuclear leukocytes to the inflammatory site. They are also useful in the treatment of asthma.

INFORMATION DISCLOSURE

U.S. Pat. No. 4,388,312 discloses benzoquinones and benzo-hydroquinones that possess inhibitory action of SRS-A (slow reacting substance of anaphylaxis). U.S. Pat. No. 4,407,757 discloses aralkyl carboxylic acid compounds that have action on lysosomal membranes of cells and physiologic host defense control activity. Additional references for these patents include European Patents 38160 and 124379; Japanese Patent No. J8 4018379.

M. Shiraishi and S. Terao, J. Chem. Soc. Perkin Trans I, 1591–1599 (1983) discloses a series of quinone and naphthalene derivatives with alkenyl and alkynyl groups in the side chain, including 3-(12-hydroxydodeca-5,10-diynyl)-1,4-dimethoxy-2-methylnaphthalene. It was found that quinone derivatives, such as 2-(12-h-ydroxydodeca-5,10-diynyl)-3,5,6-trimethyl-1,4-benzoquinone, are inhibitors of leukotrienes and 5-HETE formation from arachidonic acid.

T. Yoshimoto, et al. Biochim. Biophys. Acta. 713: 470 (1982); Y. Ashida, et al. Prostaglandins 26: 955 (1983); K. Ohuchi, et al. Prostaglandins, Leukotrienes and Medicine 12: 175 (1983); and M. Shiraishi, et al. J. Pharmacobiodyn 7: S-95 (1984); S. Yamamoto, et al., J. Allergy Clin. Immunol. 74: 349 (1984) found Takeda's diyne AA-861 (2-(12-hydroxydodeca-5,10-diynyl)-3,5,6-trimethyl-1,4-benzoquinone) one of the most potent and specific inhibitors of the biosynthesis of leukotrienes of the compounds studied.

Other patents in this area have been limited to the benzoquinone ring system: Eisaii KK—Japanese Patent Nos. J8 4038204 to J8 4038206 and J8 4025792; Nisshin Flour Mill KK—Japanese Patent No. J8 4030690.

Derwent Basic Abstract, Accession Number 92102D, discloses substituted phenone, quinone and benzene compounds that are useful for treating myocardial and cerebral tissue disturbances.

Derwent Basic Abstracts, Accession Numbers 73650E and 78090E, disclose treating diseases caused by slow reacting anaphylaxis material by administering quinone compounds.

Derwent Basic Abstract, Accession Number 62130K, discloses coronary vasodilator quinone compounds used for treatment of such conditions as myocardial infarction and atherosclerosis.

Derwent Basic Abstract, Accession Numbers 83-789978, 83-823261 and 83-823262, disclose dimethoxy-methyl-hydroxy or carbonyl-alkyl benzoquinone derivatives.

Derwent Basic Abstract, Accession Number 83-802692, discloses 2,3,5-tri-substituted -6-methyl-1,4-benzoquinone derivatives which are useful as inhibitors of proto-collagen-proline hydroxylase and 5-lipoxidase.

Derwent Basic Abstracts, Accession Numbers 84-052398 and 84-077077, disclose (hydro)quinone compounds with anti-asthma, antiallergy and antiarteriosclerosis activity.

Derwent Basic Abstract, Accession Number 84-108977, discloses 6,8-dihydroxy-7-methyl-1,4-naphthoquinones useful for inhibiting animal tissue fibrosis.

Derwent Basic Abstract, Accession Number 84-277605, discloses new 2,3-dimethoxy-5-methyl-hydroquinone and/or 4 sulphate derivatives having, e.g., antioxidative action on lipids, immunoregulating and phosphodiesterase inhibiting activity.

Derwent Basic Abstract, Accession Number 83-44366K, discloses new naphthoquinone derivatives which are useful as intermediates in producing Vitamin/K compounds.

Derwent Basic Abstract, Accession Number 85-138989, discloses 1,4-benzoquinone derivatives which are useful as SRS-A inhibitors.

SUMMARY OF THE INVENTION

The present invention provides:

(1) a compound having the formula I, II, III or IV wherein $R_1$ is
(a) hydrogen,
(b) —C(O)—($C_1$-$C_4$)alkyl,
(c) a residue of an amino acid,
(d) a side chain of an amino acid,
(e) —C(O)—$(CH_2)_q$—C(O)—OR$_3$—,
(f) cis and trans —C(O)—CH=CH—C(O)—OR$_3$,
(g) —benzoyl—$CO_2R_3$,
(h) tetrahydro-2H-pyranyl,
(i) trimethylsilyl,
(j) t-butyldimethylsilyl, or
(k) —$CH_2CH=CH_2$;

wherein $R_3$ is hydrogen, ($C_1$-$C_4$)alkyl or a pharmacologically acceptable cation, q is 0 to 8, inclusive, n is 0 to 4, inclusive;

$R_2$ is
(a) —Y—$(CH_2)_m$—Y—$(CH_2)_p$—$X_1$,
(b) —OH,
(c) tetrahydropyran-2-yloxy,
(d) —CHO,
(e) —CH=$CH_2$,
(f) hal, or
(g) hydrogen;

wherein Y is —$CH_2CH_2$—, —CH=CH—, or —C≡C—, $X_1$ is —$CH_2OR_1$, $CO_2R_3$ or —$CH_2$—hal, wherein hal is chlorine, bromine or iodine, m is 1 to 5, inclusive, and p is 0 to 3, inclusive;

with the provisos that: (1) when $R_2$ is —CH=$CH_2$, n is 1 and $R_1$ is hydrogen or tetrahydro-2H-pyranyl; and (2) when n is 0, $R_1$ is —$CH_2CH$=$CH_2$ and $R_2$ is hydrogen;

(2) A process for preparing compounds of claim 1;

(3) intermediates used in the process for preparing compounds of claim 1 having the formula 2-(11-hydroxyundeca-4,9-diynyl)-1-hydroxy-4-methoxynaphthalene;

(4) therapeutic use of compounds I, II, III and IV to inhibit 5-lipoxygenase and leukotriene biosynthesis; and (5) therapeutic use of compounds I, II, III and IV as antiinflammatory agents.

The prefix $C_1$-$C_4$ alkyl refers to alkyl of 1 to 4 carbon atoms, inclusive, and means methyl, ethyl, propyl, and butyl and isomeric forms thereof.

The term "residue of an amino acid" and "side chain of an amino acid" means the dehydroxylated form (—C(O)CH($NH_2$)$R_0$) and decarboxylated form (—$CH_2$CH($NH_2$)$R_0$), respectively, of those acids wherein $R_0$ is chosen so as to encompass all commonly available amino acids including the naturally occurring acids such as: glycine, alanine, valine, leucine, isoleucine, phenylalanine, lysine, proline, tryptophan, methionine, serine, threonine, cysteine, tyrosine, asparagine, glutamine, aspartic acid, glutamic acid, arginine, ornithine, and histidine, and synthetic derivatives thereof. These compounds may be in L or D configuration and are well known and readily available to those skilled in the art.

The pharmacologically acceptable salts are those compounds wherein $R_3$ is a pharmacologically acceptable metal cation. Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron and primary, secondary, or tertiary amines are included. Examples of suitable amines are methylamine, dimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.:

1-methylpiperidine,
4-ethylmorpholine,
1-isopropylpyrrolidine,
2-methylpyrrolidine,
1,4-dimethylpiperazine,
2-methylpiperidine, and the like, as well as amines containing water-solubilizing or hydrophilic groups, e.g.:

mono-, di-, and triethanolamine,
ethyldiethanolamine,
N-butylethanolamine,
2-amino-1-butanol, 2-amino-2-ethyl-1,3-propanediol,
2-amino-2-methyl-1-propanol,
tris(hydroxymethyl)aminomethane,
N-phenylethanolamine,
N-(p-tert-[amyl]phenyl)diethanolamine,
galactamine,
N-methylglycamine,
N-methylglucosamine,
ephedrine,
phenylephrine,
epinephrine,
procaine,
and the like. Further useful amine salts are the basic amino acid salts, e.g.:
lysine and
arginine.

Examples of suitable pharmacologically acceptable quaternary ammonium cations are:
tetramethylammonium,
tetraethylammonium,
benzyltrimethylammonium,
phenyltriethylammonium, and the like.

The compounds of the present invention will be named herein using the Chemical Abstracts numbering system (see Naming and Indexing of Chemical Substances for Chemical Abstracts during the Ninth Collective Period (1972–1976), a reprint of section IV from the Volume 76 Index Guide). The cis and trans configurations of the compounds of the present invention will be named herein as the Z and E isomers, respectively.

Compounds of this invention have been tested in one or more standard laboratory tests which demonstrate 5-lipoxygenase and leukotriene inhibiting activity. Such tests are known to those skilled in the art.

To demonstrate the SRS-A inhibitory activity of the compounds of this invention, compounds of this invention were evaluated in a standard laboratory test. This test is conducted in rat mononuclear cells incubated in the presence of cysteine and challenged with a calcium ionophore (which induces SRS-A formation).

Some of the compounds of the present invention were also tested for lipoxygenase inhibition. Arachidonic acid is added to washed human platelets and the oxygen uptake is measured using oxygraph cells. A decrease of oxygen uptake versus the control cell indicates inhibition of lipoxygenase. For a full description of the procedure see, Wallach, et al., Biochim, Biophys. Acta. 231: 445 (1976).

In general, the preferred compounds of this invention are those of the formula I wherein $R_1$ is H, $-C(O)CH_3$, $-C(O)C(isopropyl)H-NH_2$, $C(O)-CH_2)_2CO_2H$; $R_2$ is $C\equiv C-(CH_2)_3-C\equiv C-CH_2OR_1$ and n is 3 or 4.

All of the compounds of this invention are useful as lipoxygenase inhibiting agents.

The compounds of this invention may exhibit varying degrees of thromboxane $A_2$ synthetase inhibiting activity and/or cyclo-oxygenase inhibiting activity as well. As such these compounds are useful in preventing or inhibiting the production of mucus in warm blooded animals, including humans. For many of the intended applications, this combination of effects may be desirable. The novel analogs of this invention are useful in the treatment of asthma, and are useful, for example, as broncodilators or as inhibitors of mediators, such as SRS-A, and histamine which are released from cells activated by an antigen-antibody complex. Thus, these compounds control spasm and facilitate breathing in conditions such as brochial asthma, brochitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously, or intramuscularly; with intravenous administration being preferred in emergency situations; by inhalation in the form of aerosols or solutions for nebulizers; or by insufflation in the form of powder. Doses in the range of about 0.01 to 5 mg/kg of body weight are used 1 to 4 times a day, the exact dose depending on the age, weight, condition of the patient and on the frequency and route of administration. For the above use these compounds can be combined advantageously with other antiasthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The compounds of this invention will be useful as anti-inflammatory agents in mammals and especially humans, and for this purpose, are administered systemically and preferably orally. For oral administration, a dose range of 0.05 to 50 mg/kg of human body weight is used to give relief from pain associated with inflammatory disorders such as rheumatoid arthritis. They are also administered intravenously in aggravated cases of inflammation, preferably in a dose range of 0.01 to 100 μg/kg/minute until relief from pain is attained. When used for these purposes, these novel compounds cause fewer side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

The compounds of this invention are also useful for inhibiting or preventing the hypersecretion of mucus in the airways or the respiratory tract of a patient in need thereof. More particularly, the present invention provides a method for inhibiting or preventing the hypersecretion of mucus in the respiratory tract of patients with bronchial asthma, chronic bronchitis, cystic fibrosis, bronchorrhea, obstructive bronchitis and other disease conditions associated with hyperplasia of mucus secreting cells and increased mucus secretion. The method of the present invention finds particular use in warm blooded animals including mammals, such as cattle, horses, rodents, dogs, sheep, pigs, monkeys, cats, humans, and birds. The present invention provides a prophylactic as well as therapeutic method of treating hypersecretion of mucus in the airways of a warm blooded animal.

In practicing the method of inhibiting mucus secretion the quantity of compound of Formula I, II, III or IV to be administered is any amount effective in inhibiting or preventing hypersecretion of mucus in the airways of the patient being treated. The compounds of Formula I, II, III or IV are administered, e.g., intravenously, intramuscularly, topically, by aerosol inhalation, bucally or orally. The quantity of compound of Formula I, II, III or IV effective in achieving the method here claimed is determined by the particular mode of administration and frequency of administration as well as the age and condition of the patient. Generally the amount of compound administered will range from about 0.01 mg to 10 mg per dose given up to three times per day by aerosol inhalation. For intravenous administration a dose of about 0.01 to 10 μg/kg/min is administered with intramuscular injection ranging from 0.5 to 15 mg per dose. For oral administration unit doses of from 2 mg to 50 mg given up to three times per day of compounds of Formula I, II, III or IV are effective in practicing the method of the present invention. The quantity of compound applied topically is that which will give comparable blood levels of active ingredient when said substance is administered by any of the other various routes of administration.

GENERAL DESCRIPTION OF PROCESS

Compounds of the invention of Formula I, II, III and IV are prepared in accordance with processes illustrated schematically in Charts A, B, C, D, E and F.

In Step 1 of Chart A, Scheme 1, the alcohol A-1 is converted to the corresponding halide A-2 wherein X is chloride, bromide or iodide by (a) reacting it with methanesulfonylchloride in the presence of a solvent and base and (b) reacting the mesylate formed in (a) with an alkali halide in the presence of a solvent. The mesylate formation can be conducted at a temperature of about $-50°$ to $30°$ C. and for a period of about 1 to 24 hours. Solvents that can be used include methylene chloride and dichloroethane. Bases that can be used include calcium carbonate and triethylamine. Reaction of the mesylate with the alkali halide is conducted at a temperature of about $0°$ to $75°$ C. for a period of about 1 to 72 hours. Solvents that can be used include acetone, methylethylketone and 3-pentanone. The preferred alkali halide is sodium iodide.

In Step 2, the halide A-2 is reacted with 1-(tetrahydropyran-2-yloxy)-octa-2,7-dyne, a known compound, in the presence of a base at a temperature of about $-50°$ to $50°$ C. for a period of about 1 to 24 hours to form protected diyne A-3. The molar ratio of halide to diyne is about 1:1 to 1:2. Bases that can be used include sodium amide, butyllithium, lithium diisopropylamide (LDA), Grignard reagents and lithium bis(trimethylsilyl)amide LIN(TMS)$_2$. The preferred base is butyllithium.

In Step 3, the methoxy diyne A-4 is prepared by subjecting the protected diyne A-3 to deprotection. Deprotection can be accomplished by methods well known in the art. For example, the protected diyne A-3 can be warmed in the presence of p-toluenesulfonic acid at a temperature of between $0°$ and $50°$ C. for a period of about 1 to 12 hours. The methoxy diyne A-4 can be recovered from the reaction mixture by methods well known in the art.

In Step 4, amino acid ester A-5 and acid salts thereof are prepared from the diyne A-4. The protected ester A-5a is prepared by reacting a solution of the diyne A-4 in N,N-dicyclohexylcarbodiimide and 4-dimethylaminopyridine with N-t-butyloxycarbonyl-valine in accordance with the procedure described by Hassner and Alexanian, Tet. Lett., 4475 (1978).

The protected ester A-5a is deprotected to A-5b by methods well known in the art. For example, the protected valine ester can be deprotected by reacting a solution of it in methylene chloride with trifluoroacetic acid.

The acid salt A-5c is prepared by reacting the deprotected acid A-5b with the appropriate mineral or organic acid in accordance with methods well known in the art. For example, the hydrochloride salt can be prepared by bubbling anhydrous hydrogen chloride gas through a solution of the deprotected valine ester.

Compounds of Formula I wherein $R_1$ is —C(O)CH$_2$CH$_2$CO$_2$R$_3$ and $R_2$ is —C≡C—(CH$_2$)$_3$—C≡CCH$_2$OC(O)CH$_2$CH$_2$CO$_2$R$_3$ can be prepared in accordance with the process illustrated in Chart B. The free acid B-2a can be prepared by reacting the dialcohol B-1 (A-4) with carboxylic acid anhydride. This reaction can be conducted under conditions well known in the art for acylating hydroxy groups. The preparation of salts from the free acids is accomplished by reaction with bases that will provide pharmaceutically acceptable cations in accordance with methods well known in the art. For example, the potassium salt B-2b and THAM salt B-2c are prepared by reacting the free acid with potassium carbonate and tris-(hydroxymethyl)aminomethane, respectively.

The naphthoquinone of Formula II can be prepared from the compounds of Formula I in accordance with the process illustrated in Chart C. In Chart C, a solution of the diol derivative C-1 (A-4) is reacted with ceric ammonium nitrate in an acetonitrile/water mixture to yield naphthoquinone C-2.

The alcohols A-1 used as starting material in Scheme 1 of Chart A can be prepared by the process illustrated in Charts D and E.

Scheme D is utilized to prepare the starting alcohol A-1 wherein n is 3. In Step (1), 4-methoxy-1-naphthol (D-1), a known material, in a suitable solvent is reacted with sodium hydride and then with allyl bromide to provide the propenyloxy compound D-2. The reaction of the naphthol and sodium hydride is conducted at a temperature of about $0°$ to $50°$ C. for a period of about 0.2 to 5 hours. Solvents that can be used include dimethylformamide (DMF), tetrahydrofuran (THF), dimethylsulfoxide (DMSO) and N-methyl-pyrrolidone (NMP). The preferred solvent is DMF. The alkylation with allyl bromide is conducted at a temperature of about $0°$ to $50°$ C. and for a period of 0.2 to 5 hours.

The propenyloxy compound D-2 is then heated to Step 2 with N,N-dimethylaniline at a temperature of about $150°$ to $200°$ C. to provide 4-methoxy-2-(2-propenyl)-naphthalenol D-3 which can be separated from the reaction mixture by conventional means.

In Step 3, the naphthalenol D-3 is converted to a protected form D-4 using procedures known in the art. Protecting groups that can be used include tetrahydropyranyl, trimethylsilyl and t-butyldimethylsilyl. The preferred protecting group is tetrahydropyranyl. The protected naphthalenol D-4 can be recovered from the reaction mixture utilizing conventional means such as extraction, crystallization, evaporation, chromatography and combinations thereof.

The alcohol D-5 (A-1) is obtained in Step 4 by treating a solution of the protected naphthalenol D-4 with 9-Borabicyclo[3.3.1]nonane (9-BBN) in tetrahydrofuran and then treating the resulting solution with hydrogen peroxide/sodium hydroxide. The alcohol D-5 can be recovered from the reaction mixtur by conventional means such as crystallization, extraction, evaporation, chromatography and combinations thereof.

Scheme E illustrates the preparation of starting alcohol A-1 wherein n is 4 by chain extension of the alcohol A-1 wherein n is 3. In Step (1) a solution of the alcohol E-1 in methylene chloride is reacted with a solution prepared by reacting a solution of oxalyl chloride in methylene chloride and DMSO at $-60°$ C. to approximately $-70°$ C. The resulting mixture is then treated with triethylamine to yield the aldehyde E-2. The aldehyde E-2 is recovered from the reaction mixture by conventional means.

In Step 2 the aldehyde E-2 is reacted with ylide generated from methoxymethyl triphenylphosphonium chloride in the presence of a base (e.g., n-butyllithium) and solvent to produce the 2-methoxybutenyl compound E-3. The reaction is conducted at a temperature of about −10° to 40° C. for a period of about 0.2 to 5 hours. Solvents that can be used include tetrahydrofuran, diethylether, hexane, dimethylether, DMSO and NMP.

In Step 3, the 2-methoxybutenyl compound E-3 is converted to the aldehyde E-4 by methods well known in the art.

In Step 4, the hydroxy group of the aldehyde E-4 is protected by methods known to those skilled in the art to produce the O-THP aldehyde E-5. Protecting groups include the same ones noted above.

In Step 5 the aldehyde E-5 is reduced to the alcohol E-6 by conventional means.

While the general description above and the specific embodiments illustrated below are related to 1,4-naphthalenediol and 1,4-naphthoquinone derivatives of this invention, corresponding processes and uses as they relate to the 1,4-hydroquinone and quinone derivatives of this invention can be performed by substituting the appropriate 1,4-hydroquinone derivatives and quinone derivatives for the 1,4-naphthalenediol and 1,4-naphthoquinone derivatives, respectively.

All of the compounds of this invention are prepared by the procedures described above.

DESCRIPTION OF PREFERRED EMBODIMENTS

Preparation 1:
1-Methoxy-4-(2-propenyloxy)-naphthalene (Refer to Chart D, D-1 to D-2)

A 500 ml 3-necked round bottom flask, equipped with magnetic stirring bar, nitrogen inlet, and equalizing pressure addition funnel, is charged with 4.18 g of 50% sodium hydride (dispersion in mineral oil). While purging the flask with nitrogen the solid is washed with hexane two times. The resulting gray powder is suspended in 60 ml of dimethylformamide and placed under a nitrogen atmosphere. A solution of 4-methoxy-1-naphthol (10.02 g) in 60 ml of dimethylformamide is then added dropwise via the addition funnel to the stirred hydride mixture over 5 min. Vigorous gas evolution ensues and a thick emulsion forms which stops the magnetic stirring bar. An additional 50 ml of dimethylformamide is added to help break up this emulsion. The resulting dark green colored mixture is vigorously stirred for 15 min and then allyl bromide (6.2 ml) is added dropwise over 2 to 3 min as a neat solution. Gradually the mixture dissolves to give a dark green colored solution. After stirring for 15 min at room temperature, TLC analysis confirms the alkylation is complete. The reaction is quenched with saturated aqueous ammonium chloride, water (100 ml) is added and the pH is adjusted to 7 (addition of 10% aqueous sodium bisulfate). This mixture is extracted two times with ether. The combined organic extracts are washed five times with water, dried with magnesium sulfate, filtered and concentrated to give the crude product as a reddish-brown colored oil.

This material is combined with some previously prepared lots of crude product and chromatographed over 787 g of HPLC grade silica gel eluting with 2% ethyl acetate/hexane and collecting 50 ml fractions. Fractions 48–67 are combined and concentrated to give 12.67 g of the product contaminated with a less polar impurity.

This material is then chromatographed over a gravity column containing 1260 g of silica gel packed in Skellysolve B. A gradient elution sequence is performed as shown below collecting 1000 ml fractions.

| Fraction | Eluent |
|----------|--------|
| 1–2 | Skellysolve B |
| 3–14 | 0.50% ethyl acetate/Skellysolve B |
| 15–20 | 0.75% ethyl acetate/Skellysolve B |
| 21–27 | 1.0% ethyl acetate/Skellysolve B |

At this point 400 ml fractions are collected. Fractions 31–32 are homogeneous by TLC and are combined and concentrated to give 1.34 g of the pure title product which is used for analysis. Fractions 33–47 afford 12.18 g of the title product contaminated as before with the more polar impurity. This material is used in subsequent experiments without further purification.

The pure material derived from fractions 31–32 solidified and this material is recrystallized from acetone/hexane. Upon attempting to collect the crystals by suction filtration, they partially melt to give a waxy solid which upon further standing gradually melts. This material is collected and reconcentrated. Upon concentration under high vacuum the material gradually solidifies, m.p. 30.5°–32.0° C.

NMR (CDCl$_3$; TMS): $\delta$8.45–8.16; 7.63–7.40; 6.54; 6.37–5.89; 5.60–5.16; 4.60–4.42; 3.81.

Infrared (Nujol): $\nu_{max}$ 1778, 1649, 1630, 1596, 1423, 1393, 1359, 1275, 1239, 1153, 1101, 1083, 1022, 1005, 969, 924, 807 and 769 cm$^{-1}$.

Anal. Found: C, 78.35; H, 6.63.

Mass Spectrum: m/e Found: 214.0994. Other ions at m/e 173, 145, 130, 115 and 102.

TLC (Silica Gel GF): R$_f$=0.30 in 2% ethyl acetate/hexane.

Preparation 2:
4-Methoxy-2-(2-propenyl)-1-naphthalenol (Refer to Chart D, D-2 to D-3)

A 250 ml 3-necked round bottom flask, equipped with magnetic stirring bar, nitrogen inlet and condenser, is charged with 10.39 g of 1-methoxy-4-(2-propenyloxy)-naphthalene. This material is dissolved in 30 ml of N,N-dimethylaniline. The stirred solution is placed under a nitrogen atmosphere and heated to a gentle reflux (−195° C.) by use of a heating mantle. By the time reflux has been achieved, TLC analysis confirms the rearrangement is complete. The solution is cooled, diluted with ethyl acetate and crushed ice and then washed five times with 100 ml portions of 0.5N hydrochloric acid until the aqueous wash is strongly acidic. The organic extract is then washed two times with water until the aqueous wash is neutral, dried with magnesium sulfate, filtered and concentrated to give the crude title product as an orange colored oil. This material is combined with a previously prepared lot to give 11.36 g of crude material.

This material is chromatographed on 397 g of HPLC grade silica gel eluting with 5% ethyl acetate and taking 50 ml fractions. Fractions 33–55 are combined and concentrated to give a slightly impure product. This material is diluted with ethyl acetate, treated with decoloring charcoal, filtered and concentrated to give 10.14 g of material. This material is rechromatographed on 390 g of HPLC grade silica gel eluting with 5% acetone/hexane and taking 45 ml fractions. Fractions 35–39 are homgeneous by TLC and are combined and concentrated to give 9.72 g of the title compound. This material later solidifies, m.p. 45.0°–46.5° C.

NMR (CDCl$_3$; TMS): $\delta$ 8.33–8.05; 7.60–7.33; 6.53; 6.39–5.79; 5.32–5.03; 5.10; 3.90; 3.58–3.38.

Infrared (Nujol): $\nu_{max}$ 3253, 1634, 1600, 1270, 1229, 1166, 1121, 1085, 1032, 988, 957, 907, 848, 760 and 646 cm$^{-1}$.

Anal. Found: C, 78.30; H, 6.56.

Mass Spectrum: m/e Found: 214.0983. Other ions at m/e 199, 181, 171, 157, 128 and 115.

TLC (Silica Gel GF): R$_f$=0.27 in 10% acetate/hexane.

Preparation 3:

Tetrahydro-2-[[4-methoxy-2-(2-propenyl)-1-naphthalenyl]oxy]-2H-Pyran (Refer to Chart D, D-3 to D-4)

A solution of 4-methoxy-2-(2-propenyl)-1-naphthalenol (0.28 g), dihydropyran (0.60 ml) and pyridinium hydrochloride (32 mg) all in 5 ml of methylene chloride is stirred under a nitrogen atmosphere for 16 hrs at which time TLC analysis indicates the reaction is complete. The solution is poured into 25 ml of saturated aqueous sodium bicarbonate and extracted with ether. The organic phase is washed two times with brine, dried with magnesium sulfate, filtered and concentrated to give 0.42 g of crude product as a yellow oil.

This material is chromatographed on 55 g of HPLC grade silica gel eluting with 5% ethyl acetate/hexane and collecting 30 ml fractions. Fractions 5–6 are homogeneous by TLC and are combined and concentrated to give 0.325 g of title compound.

NMR (CDCl$_3$; TMS): $\delta$ 8.34–8.02; 7.65–7.30; 6.65; 6.34–5.81; 5.31–4.83; 4.27–3.88; 3.96; 3.77–3.30; 2.23–1.37.

Infrared (film): $\nu_{max}$ 3075, 2944, 2851, 1628, 1598, 1509, 1460, 1367, 1264, 1229, 1204, 1164, 1105, 1082, 1065, 1035, 989, 944, 905, 846 and 768 cm$^{-1}$.

Anal. Found: C, 75.89; H, 7.44.

Mass Spectrum: No M$^+$.Base peak at m/e 214 (M$^+$-THP+H).

Other ions at m/e 199 and 85.

TLC (Silica Gel GF): R$_f$=0.38 in 10% ethyl acetate/hexane.

Preparation 4:

3-[4-Methoxy-1-[(tetrahydro-2H-pyran-2-yl)oxy]-2-naphthalenyl]-1-propanol (Refer to Chart D, D-4 to D-5)

A 100 ml 2-necked (14/20) round bottom flask, equipped with magnetic stirring bar, nitrogen inlet and serum cap, is charged with a solution of tetrahydro-2[[4-methoxy-2-(2-propenyl)-1-naphthalenyl]oxy]-2H-pyran (0.54 g) in 10 ml tetrahydrofuran. The solution is placed under a nitrogen atmosphere, cooled to 0°–5° C. and then treated with 13.4 ml of 0.5M 9-BBN in tetrahydrofuran. The ice bath is removed and the solution is stirred at room temperature for 1.25 hrs. Again the solution is cooled to 0°–5° C. and 0.5 ml water is added followed by the addition of 2.2 ml 3N sodium hydroxide and 2.2 ml 30% hydrogen peroxide. The ice bath is removed and the solution is stirred at room temperature for 45 min at which time TLC analysis indicates no remaining starting material. The solution is poured into 50 ml water, neutralized to pH 7 with 10% aqueous sodium bisulfate and extracted two times with ethyl acetate. The organic extracts are combined, washed with brine, dried with magnesium sulfate, filtered and concentrated to give 1.6 g of crude product as a yellow oil.

This material is chromatographed on 55 g of HPLC grade silica gel eluting with 33% ethyl acetate/hexane (with 0.5% triethylamine present) and collecting in 45 ml fractions. Fractions 17–40 are homogeneous by TLC and are combined and concentrated to give 615 mg of product. NMR spectral analysis of this material indicates an impurity present.

This material is redissolved in 10 ml tetrahydrofuran. 3N sodium hydroxide (2 ml) and 30% hydrogen peroxide (2 ml) are added. The resulting mixture is stirred at room temperature for 2 hrs. The mixture is poured into 50 ml water and solid sodium bisulfite is added to destroy residual hydrogen peroxide. The pH is adjusted to 7 and the mixture is extracted two times with ethyl acetate. The combined organic extracts are washed with brine, dried with magnesium sulfate, filtered and concentrated to give the crude product as a yellow oil.

This material is chromatographed on 55 g of HPLC grade silica gel eluting with 20% acetone/hexane (with 0.5% triethylamine present) and collecting in 45 ml fractions. Fractions 9–11 are homogeneous by TLC and are combined and concentrated to give 409 mg of pure title compound. Fractions 12–13 affords an additional 39 mg of impure material.

NMR (CCl$_4$; TMS): $\delta$ 8.25–7.86; 7.54–7.21; 6.54; 4.91–4.85; 4.17–3.82; 3.88; 3.63–3.20; 3.10–2.70; 2.17–1.30.

Infrared (film): $\nu_{max}$ 3419, 2942, 2864, 1628, 1598, 1509, 1460, 1420, 1368, 1265, 1225, 1206, 1163, 1105, 1067, 1035, 987, 945, 906, 870, 847, 815, 769 and 700 cm$^{-1}$.

Anal. Found: C, 71.81; H, 7.73.

Mass Spectrum: m/e Found: 316.1685. Other ions at m/e 232, 214, 199, 186, 128, 115 and 85.

TLC (Silica Gel GF): R$_f$=0.34 in 33% acetone/hexane. R$_f$=0.13 in 33% ethyl acetate/hexane.

Preparation 5:

2-(2-Formylethyl)-4-methoxy-1-[(tetrahydro-2H-pyran-2-yl)oxy]naphthalene (Refer to Chart E, E-1 to E-2)

An oven-dried 25 ml 2-necked (14/20) round bottom flask, equipped with magnetic stirring bar, nitrogen inlet and serum cap, is charged with a solution of oxalkyl chloride (61 $\mu$l) in 2 ml methylene chloride. This solution is placed under a nitrogen atmosphere and cooled to $-60°$ C. to $-50°$ C. Dimethylsulfoxide (99 $\mu$l) is added (neat) dropwise to give a colorless solution. After 2–3 min a solution of 3-[4-methoxy-1-[(tetrahydro-2H-pyran-2-yl)oxy]-2-naphthalenyl]-1-propanol (0.19 g) in 1 ml methylene chloride is added drowpise. The resulting mixture is stirred at $-60°$ C. to $-50°$ C. for 15 min and then treated with triethylamine (0.44 ml). This gives rise to a yellow colored milky suspension. The cooling bath is removed and the stirred mixture is allowed to warm to room temperature at which time the mixture is diluted with water and extracted with ether. The organic phase is washed three times with water (after adjusting the pH to 7 with 10% aqueous sodium bisulfate), dried with magnesium sulfate, filtered and concentrated to give 0.18 g of the crude title compound as an orange colored oil.

NMR (CCl$_4$; TMS): $\delta$ 9.81; 8.24–8.12; 8.03–7.88; 7.58–7.24; 6.54; 4.90–4.84; 4.14–3.84; 3.90; 3.50–2.97; 2.70; 2.24–1.33.

TLC (Silica Gel GF): $R_f$=0.52 in 33% acetone/hexane.

Preparation 6:
(3EZ)-4-Methoxy-2-(4-methoxy-3-butenyl)-1-[(tetrahydro-2H-pyran-2-yl)oxy]-naphthalene (Refer to Chart E, E-2 to E-3)

A 50 ml oven-dried 2-necked (14/20) round bottom flask, equipped with magnetic stirring bar, nitrogen inlet and serum cap is charged with methoxymethyltriphenylphosphonium chloride (90%) (2.5 g). This material is suspended in 10 ml tetrahydrofuran and the resulting mixture is placed under a nitrogen atmosphere and cooled to 0°-5° C. n-Butyllithium reagent (1.65M in hexane, 4.0 ml) is added dropwise to the stirred mixture via syringe over 2-3 min. The solids gradually dissolve to give a deep red colored solution (some solids remain). This solution is stirred at 0°-5° C. for 30 min and then is treated with a solution of 2-(2-formylethyl)-4-methoxy-1-[(tetrahydro-2H-pyran-2-yl)oxy]naphthalene (0.958 g) in 5 ml tetrahydrofuran in one portion. The resulting deep red colored solution is stirred at 0°-5° C. for 15 min at which time TLC analysis indicates no remaining starting material. The solution is poured into saturated aqueous ammonium chloride, the pH adjusted to 7 with 10% sodium bisulfate and this mixture extracted first with Skellysolve B and then with ether. Each of these extracts is washed two times with water, dried with magnesium sulfate, filtered and concentrated. TLC analysis of the ether extract indicates the presence of the product mixture suggesting that the Skellysolve B extraction is not efficient. The separate extracts are combined to give 1.36 g of the title compound mixture.

This material is chromatographed on 190 g of HPLC grade silica gel eluting with 5% acetone/hexane and collecting 50 ml fractions. Fractions 16-20 are homogeneous by TLC and are combined and concentrated to give 0.437 g (40% yield) of the title compound as a mixture of E and Z isomers.

NMR (CDCl4; TMS): δ 8.30-7.96; 7.59-7.25; 6.62 and 6.55; 6.33; 5.80; 4.93-4.77; 4.80-4.25; 4.20-3.85; 3.91; 3.62-3.25; 3.50 and 3.43; 3.07-2.70; 2.62-2.15; 2.1-1.3.

TLC (Silica Gel GF): $R_f$=0.24 in 5% acetone/hexane.

Preparation 7:
2-(3-Formylpropyl)-4-methoxy-1-hydroxynaphthalene (Refer to Chart E, E-3 to E-4)

A solution of 947 mg of (3EZ)-4-methoxy-2-(4-methoxy-3-butenyl)-1-[(tetrahydro-2-H-pyran-2-yl)oxy]-naphthalene dissolved in 10 ml of 3:1:1, acetic acid:tetrahydrofuran:water is stirred at 40° C. for 3 hrs. TLC analysis still indicates unhydrolyzed starting material. The temperature is increased to 50° C. and continued stirring for 1 hr affords complete hydrolysis. The solution is poured into 25 ml water and solid sodium bicarbonate is added portionwise until gas evolution ceases. This mixture is extracted with ether and the organic phase is washed with saturated aqueous sodium bicarbonate and brine (pH adjusted to 7), dried with magnesium sulfate, filtered and concentrated to give 0.95 g of crude title product as an orange colored oil.

TLC (Silica Gel GF): $R_f$(starting material)=0.58 in 33% acetone/hexane. $R_f$(product)=0.41 in 33% acetone/hexane.

Preparation 8:
2-(3-Formylpropyl)-4-methoxy-1-[(tetrahydro-2H-pyran-2-yl)oxy]naphthalene (Refer to Chart E, E-4 to E-5)

A solution of 76 mg of 2-(3-formylpropyl)-4-methoxy-1-hydroxynaphthalene in 2 ml methylene chloride is treated with 0.5 ml of dihydropyran and then with a few mg of pyridinium hydrochloride. The resulting solution is stirred at room temperature for 24 hrs at which time TLC analysis indicates no remaining starting material. The solution is poured into 20 ml of saturated aqueous sodium bicarbonate and extracted two times with ether. The combined organic extracts are washed with water (pH adjusted to 7 with 10% aqueous sodium bisulfate), dried with magnesium sulfate, filtered and concentrated to give 173 mg of crude product.

This material is chromatographed on 7.1 g of HPLC grade silica gel eluting with 5% acetone/hexane (with 0.5% triethylamine present) and collecting 30 ml fractions. Fractions 1-2 are combined and concentrated to give 74 mg of nonpolar material while fractions 3-4 are combined and concentrated to give 49 mg of the title compound.

NMR (CCl4; TMS): δ 9.80; 8.28-7.88; 7.57-7.31; 6.55; 4.90-4.83; 4.19-3.84; 3.97; 3.58-3.25; 3.19-2.57; 2.50-2.25; 2.19-1.35.

TLC (Silica Gel GF): $R_f$=0.52 in 33% acetone/hexane.

Preparation 9:
4-[4-Methoxy-1-[(tetrahydro-2H-pyran-2-yl)oxy]-2-naphthalenyl]-1-butanol (Refer to Chart E, E-5 to E-6)

The starting 2-(3-formylpropyl)-4-methoxy-1-[(tetrahydro-2H-pyran-2-yl)-oxy]naphthalene (0.587 g) is dissolved in 5 ml methanol. This solution is placed under a nitrogen atmosphere and then cooled to 0°-5° C. and solid sodium borohydride (0.10 g) is added in one portion. Vigorous gas evolution ensues and after stirring for 30 min TLC analysis indicates the reduction is complete. The reaction is quenched with saturated aqueous ammonium chloride and then poured into water. The pH is adjusted to 2—3 (10% aqueous sodium bisulfate) and the mixture extracted with ether. The pH of the aqueous phase is raised to 7 (saturated aqueous sodium bicarbonate), excess solid sodium chloride is added and the mixture reequilibrated. The organic extract is dried with magnesium sulfate, filtered and concentrated to give the crude product as an orange colored oil.

This material is chromatographed on 59 g of HPLC grade silica gel eluting with 40% ethyl acetate/hexane (with 0.5% triethylamine) and collecting 30 ml fractions. Fractions 26-50 are homogeneous by TLC and are combined and concentrated to give the title compound.

NMR (CCl4; TMS): δ 8.23-7.82; 7.50-7.20; 6.53; 4.88-4.69; 4.19-3.81; 3.91; 3.67-3.22; 3.55; 2.92-2.63; 2.35; 2.15-1.35.

Infrared (film): $\nu_{max}$ 3397, 2940, 2860, 1628, 1598, 1508, 1459, 1368, 1264, 1224, 1205, 1168, 1105, 1066, 1034, 988, 946, 906, 871, 847, 815, 768 and 700 cm$^{-1}$.

Mass Spectrum: Weak M+ at m/e 330. Large ion at m/e 246. Other ions at m/e 228, 213, 187, 186 and 85.

TLC (Silica Gel GF): $R_f$=0.34 in 33% acetone/hexane. $R_f$=0.21 in 40% ethyl acetate/hexane.

Preparation 10:
2-(3-Iodopropyl)-4-methoxy-1-(tetrahydropyran-2-yloxy)-naphthalene (Refer to Chart A, A-1 to A-2)

(a) Mesylate formation. A mixture of methylene chloride (90 ml) and triethylamine (2.50 g) are premixed. A small amount of this (5–10 ml) is used to dissolve 3-[4-methoxy-1-[(tetrahydro-2H-pyran-2yl)oxy]-2-naphthalenyl]-1-propanol (5.08 g). The dissolved alcohol is introduced into a flame dried 250 ml 3-necked round bottom flask under nitrogen. This mixture is cooled in an ethanol-ice bath and the remainder of the methylene chloride-triethylamine mixture is added. To this cooled solution methanesulfonyl chloride (2.35 g) in 20 ml of methylene chloride is added slowly (20 minutes) followed by stirring an additional 50 minutes in an ethanol-ice bath. By TLC in 30% ethyl acetate/hexane the reaction is complete. The mixture is quenched with 80 ml of ice water and the layers separated. The organic phase is washed with cold, dilute sodium bicarbonate and brine, dried with sodium sulfate, filtered, and concentrated to provide 6.3 g of a yellow oil ($R_f=0.26$ in 30% ethyl acetate/hexane).

(b) Iodide formation. The above oil is taken up in 100 ml of acetone, and sodium iodide (4.75 g) is added in one portion. The mixture is heated to 55° C. for 3 hours. After cooling, the mixture is filtered, and the acetone is evaporated under reduced pressure. The residue is taken up in a 50% ethyl acetate/hexane mixture and washed with an aqueous 5% sodium bisulfite solution and brine, dried with sodium sulfate, filtered, and concentrated to provide 7.1 g of a yellow oil. The oil is chromatographed on 475 g of 70–230 mesh silica gel eluting with 10% ethyl acetate/hexane. Prior to chromatography the column is washed with an ethyl acetate-triethylamine (95-5) mixture and then washed further with pure ethyl acetate to remove the majority of triethylamine. An initial fraction of 1000 ml is collected followed by 20 ml fractions. Fractions 15–52 are homogeneous by TLC and are combined and concentrated to provide 5.7 g of the title compound as a yellow oil.

NMR (CDCl$_3$; TMS): $\delta$ 8.4–8.05; 7.65–7.34; 6.65; 5.0–4.85; 3.95; 3.6–3.35; 3.35–3.1; 3.1–2.85; 2.4–1.9; 1.8–1.4.

TLC (Silica Gel GF): $R_f=0.29$ in 5% ethyl acetate/hexane.

Preparation 11:
2-(4-Iodobutyl)-4-methoxy-1-(tetrahydropyran-2-yloxy)-naphthalene (Refer to Chart A, A-1 to A-2)

(a) Mesylate formation. 4-[4-Methoxy-1-[(tetrahydro-2H-pyran-2-yl)oxy]-2-naphthalenyl]-1-butanol (0.599 g) is dissolved in 10 ml of methylene chloride and cooled in an ethanol-ice bath with the mixture under nitrogen. A mixture of triethylamine (0.279 g) in 2 ml of methylene chloride is added rapidly, followed by the slow addition (10 minutes) of methanesulfonyl chloride (0.267 g) in 2 ml of methylene chloride. Stirring is continued an additional 50 minutes with the contents cooled in an ethanol-ice bath. The reaction is quenched by the addition of ice water and separation of the layers. The organic layer is washed with a cold, dilute aqueous sodium bicarbonate solution and brine, dried with magnesium sulfate, filtered, and concentrated to provide 0.779 g of a yellow oil.

(b) Iodide formation. The above oil is dissolved in 12 ml of acetone and treated with sodium iodide (0.549 g). The mixture is heated under nitrogen to 50°–55° C. for 3 hours. After cooling, the mixture is filtered and the acetone evaporated under reduced pressure. The residue is taken up in a 50% ethyl acetate/hexane mixture, and the organic solution is washed with an aqueous 5% sodium bisulfite solution and brine, dried with magnesium sulfate, filtered, and concentrated to afford 0.712 g of a yellow oil.

The oil is chromatogrphed on 85 g of HPLC silica gel eluting with 3% ethyl acetate/hexane. An initial fraction of 180 ml is collected followed by 8 ml fractions. Fractions 37–66 are homogeneous by TLC and are collected and concentrated to provide 0.533 g of the title compound as a yellow oil.

NMR (CDCl$_3$; TMS): $\delta$ 8.35–8.0; 7.6–7.25; 6.55; 4.95–4.75; 3.85; 3.55–2.6; 2.15–1.3.

TLC (Silica Gel GF): $R_f=0.42$ in 5% ethyl acetate/hexane.

Preparation 12:
2-(11-Tetrahydropyran-2-yloxyundeca-4,9-diynyl)-1-(tetrahydropyran-2-yloxy)-4-methoxynaphthalene (Refer to Chart A, A-2 to A-3)

The 1-(tetrahydropyran)-2-yloxy)-octa-2,7-diyne (12.1 g) is dissolved in 100 ml of dry tetrahydrofuran and added to a flame dried 500 ml three-necked round bottom flask with the contents under nitrogen. The solution is cooled in an ice bath and an n-butyllithium solution (22 ml of a 2.6M solution in hexane) is added dropwise. After complete addition the solution is stirred another 45 minutes. The mixture is further cooled in an ethanol-ice bath and hexamethylphosphoramide (20.2 g) is added. The compound 2-(3-iodopropyl)-4-methoxy-1-(tetrahydropyran-2-yloxy)-naphthalene (15.7 g) is taken up in 100 ml of dry tetrahydrofuran and introduced slowly (15 minutes) to the cooled solution. After complete addition the mixture is warmed to room temperature and stirred an additional hour. By TLC in 10% ethyl acetate/hexane the reaction is complete.

The reaction is quenched by pouring into ice water. The mixture is extracted three times with a 50% ethyl acetate/hexane mixture. The organic layer is washed with water and brine, dried with sodium sulfate, filtered, and concentrated to provide 36.7 g of a yellow oil. Chromatography is carried out on 3000 g of 70–230 mesh silica gel eluting with 10% ethyl acetate/hexane, containing 0.75% triethylamine. At least 20 liters of solvent is passed through before the desired product comes off. The following 9 liters contain the desired material as indicated by TLC. Solvent evaporation gives 16.2 g of the title compound as a light yellow oil.

NMR (CDCL$_{33}$; TMS): $\delta$ 8.4–8.1; 7.7–7.4; 6.75; 5.05–4.75; 4.35–4.15; 4.0; 3.7–3.35; 3.1–2.8; 2.5–1.4.

TLC (Silica Gel GF): $R_f=0.21$ in 10% ethyl acetate/hexane.

Preparation 13:
2-(12-Tetrahydropyran-2-yloxydodeca-5,10-diynyl)-1-(tetrahydropyran-2-yloxy)-4-methoxynaphthalene (Refer to Chart A, A-2 to A-3)

The sodium amide is formed using 10 ml of ammonia condensed into a flame dried 3-necked round bottom flask. To this is added sodium metal (83.6 mg) and ferric nitrate (3 mg). After formation of the sodium amide the ammonia is evaporated using a positive nitrogen pressure with a potassium hydroxide tube functioning as the outlet vent. The resulting gray powder is covered with 2.5 ml of dry tetrahydrofuran under nitrogen followed by slow addition (15 minutes) of 1-(tetrahydropyran)-2- yloxy)-octa-2,7-diyne (0.333 g) in 3 ml of dry tetrahydrofuran. The mixture is heated to 50° C. for 75 minutes. The mixture is cooled and placed in an ethanol-ice bath. This is followed by addition of hexamethylphosphoramide (1 ml) and 2-(4-iodobutyl)-4-methoxy-1-(tetrahydropyran-2-yloxy)-naphthalene (0.533 g) in 3 ml of dry tetrahydrofuran over a 10 minute period. The mixture is warmed to room temperature and stirred an additional hour. The reaction is quenched by the addition of ammonium chloride in water followed by extraction with pentane. The organic layer is washed with water and brine, dried with sodium sulfate, filtered, and concentrated to give 0.740 g of a yellow oil.

The oil is chromatographed on 85 g of HPLC grade silica gel eluting with 8% ethyl acetate/hexane. An initial fraction of 150 ml is collected, followed by 8 ml fractions. Fractions 67–120 are homogeneous by TLC and are collected and concentrated to provide 0.396 g of the title compound as a light yellow oil.

EXAMPLE 1

2-(11-Hydroxyundeca-4,9-diynyl)-1-hydroxy-4-methoxynaphthalene (Refer to Chart A, A-3 to A-4)

2-(11-Tetrahydropyran-2-yloxyundeca-4,9-diynyl)-1-(tetrahydropyran-2-yloxy)-4-methoxynaphthalene (0.92 g) is taken up in a 50% tetrahydrofuran/methanol mixture and p-toluenesulfonic acid monohydrate (75 mg) is added. The mixture is warmed to 65° C. for 30 minutes. Upon cooling solid sodium bicarbonate (82 mg) is added and the methanol evaporated under reduced pressure. The residue is taken up in ethyl acetate and washed with water and brine, dried with magnesium sulfate, filtered and concentrated to provide 0.91 g of a yellow-orange oil.

The oil is chromatographed on 85 g of HPLC silica gel eluting with 25% ethyl acetate/hexane. A first fraction of 175 ml is collected followed by 8 ml fractions. Fractions 68–103 are homogeneous by TLC and are combined and concentrated to give 0.558 g of the title compound as a reddish-brown oil. After standing in the refrigerator the oil becomes a solid, mp 71°–73° C.

NMR (CDCl$_3$; TMS): δ 8.3–8.05; 7.6–7.3; 6.55; 6.18; 4.35–4.1; 3.9; 3.35–3.1; 2.95–2.6; 2.45–1.45.

Infrared (Nujol): $\nu_{max}$ 3312, 3205, 3078, 3006, 1598, 1398, 1388, 1360, 1311, 1277, 1234, 1218, 1121, 1094, 1027, 1016, 827, 764, 646, 625 cm$^{-1}$.

Ultraviolet: $\lambda_{max}$ (ethanol) 211, 244, 311, 320, 330.

Anal. Found: C, 78.20; H, 7.45.

TLC (Silica Gel GF): R$_f$=0.19 in 25% acetone/hexane.

EXAMPLE 2

2-(12-Hydroxydodeca-5,10-diynyl)-1-hydroxy-4-methoxynaphthalene (Refer to Chart A, A-3 to A-4)

The 2-(12-tetrahydropyran-2-yloxydodeca-5,10-diynyl-1-(tetrahydropyran-2-yloxy)-4-methoxynaphthalene (0.396 g) is dissolved in 50% methanol/tetrahydrofuran (5 ml) and para-toluenesulfonic acid monohydrate (39 mg) is added. The mixture is heated to 60° C. for 35 minutes at which time TLC indicates complete reaction. After cooling, solid sodium bicarbonate is added, and the solvent is evaporated under reduced pressure. The residue is taken up in ethyl acetate and washed with water and brine, dried with magnesium sulfate, filtered, and concentrated to provide 0.335 g of a yellow oil.

The oil is chromatographed on 35 g of 70–230 mesh silica gel eluting with 30% ethyl acetate/hexane. An initial fraction of 125 ml is collected, followed by 5 ml fractions. Fractions 19–30 are homogeneous by TLC, but fractions 31–65 are a mixture. The impure fractions are collected and concentrated and chromatographed again on 20 g of HPLC grade silica gel eluting with 25% ethyl acetate/hexane. An initial fraction of 140 ml is collected, followed by 3 ml fractions. Fractions 7–20 are homogeneous by TLC and are combined with the other pure material and concentrated to give 0.203 g of the title compound as a flaky yellow solid, mp 85°–87° C.

NMR (d$_6$ acetone; TMS): δ 8.35–8.1; 7.6–7.35; 6.75; 4.2; 3.95; 3.25; 2.95–2.75. 2.4–1.4.

Infrared (Nujol): $\nu_{max}$ 3316, 3216, 3190, 3070, 3055, 1601, 1438, 1430, 1335, 1265, 1195, 1156, 1121, 1093, 1016, 756, 653, and 617 cm$^{-1}$.

Ultraviolet: $\lambda_{max}$ (ethanol) 211, 244, 311, 320, 330.

Anal. Found: C, 77.25; H, 7.46.

Mass Spectrum: m/e Found: 350.1870.

EXAMPLE 3

2-(11-Hydroxyundeca-4,9diynyl)-1hydroxy-4-methoxynaphthalene, bis-(N-Boc valine ester) (Refer to Chart A, A-4 to A-5a)

A solution of 2-(11-hydroxyundeca-4,9diynyl)-1-hydroxy-4-methoxy-naphthalene (61.5 mg), N,N-dicyclohexylcarbodiimide (83.7 mg), 4-dimethylaminopyridine (3.3 mg), and N-t-butyloxycarbonyl(boc)(valine) (87.7 mg) in methylene chloride is initially stirred in an ice bath under nitrogen and then allowed to warm to room temperature overnight. The solution becomes milky white during this time. The contents are filtered through a cotton plug and the organic layer washed with water and brine, dried with sodium sulfate, filtered, and concentrated to give a yellow-white solid. The solid is taken up in 30% ethyl acetate/hexane and again passed through a cotton plug to remove solids. Solvent evaporation gives a yellow oil.

The above oil is chromatographed on 17 g of HPLC grade silica gel eluting with 15% acetone/hexane. An initial fraction of 45 ml is collected followed by 2½ ml fractions. Fractions 17–28 are homogeneous by TLC and are combined and concentrated to provide 116 mg of the title compound as an amorphous yellow solid.

NMR (CDCl$_3$; TMS): δ 8.35–8.15; 7.8–7.35; 6.7; 5.3–4.95; 4.8–4.65; 4.7–4.5; 4.35–4.1; 3.95; 2.85–2.45; 2.45–1.5; 1.5; 1.45; 1.25–1.05; 1.0–0.08.

Infrared (CHCl$_3$): $\nu_{max}$ 3430, 2960, 2925, 1740, 1705, 1490, 1460, 1365, 1150 cm$^{-1}$.

TLC (Silica Gel GF): R$_f$=0.41 in 25% acetone/hexane and R$_f$=0.58 in 10% isopropanol/hexane.

EXAMPLE 4

2-(11-Hydroxyundeca-4,9-hydroxy-4-methoxynaphthalene, bis-(valine ester) (Refer to Chart A, A-5a to A-5b).

A 15 ml one-necked round bottom flask was flame dried and placed under a nitrogen atmosphere. This flask was charged with 2-(11-Hydroxyundeca-4,9-diynyl)-1-hydroxy-4-methoxynaphthalene, bis(N-t-butyloxycarbonyl valine ester) (0.105 g) in 3 ml of methylene chloride via syringe. The solution is cooled in an ice bath and trifluoroacetic acid (1.5 ml) is added via syringe. The solution is kept in the ice water bath 10 minutes and allowed to warm to room temperature over a period of 75 minutes, at which time TLC indicates the reaction is complete.

The solution is concentrated under reduced pressure and taken up in ethyl acetate. A smaller amount of the valine ester (5.9 mg) is reacted in a similar fashion and combined with the material from this experiment. The organic solution is washed with water, saturated sodium bicarbonate, water, and brine, dried with sodium sulfate, filtered, and concentrated to give 71.4 mg of a yellow oil. The above oil is chromatographed on 8 g of HPLC grade silica gel eluting with 20% hexane/ethyl acetate (with 0.5% triethylamine). An initial fraction of 10 ml is collected followed by 2.5 fractions. Fractions 15–51 are homogeneous by TLC and are combined and concentrated to provide 53.5 mg of the title compound as a clear oil. The NMR for the chromatographed oil is identical to that for the previous yellow oil and TLC still indicates the presence of some impurities.

NMR (CDCl$_3$; TMS) $\delta$ 8.4–8.2; 7.85–7.45; 6.75; 4.85–4.7; 4.05; 3.85–3.75; 3.35–3.25; 2.85–2.6; 2.55–1.5; 1.65; 1.3–1.1; 1.0–0.8.

Mass Spectrum: m/e Found: 534.3089.

TLC (Silica Gel GF): R$_f$=0.38 in 0.59% triethylamine/ethyl acetate.

EXAMPLE 5

2-(11-Hydroxyundeca-4,9-diynyl)-1-hydroxy-4-methoxynaphthalene, bis-(valine ester, hydrochloride)
Refer to Chart A, A-5b to A-5c)

The starting material 2-(11-hydroxyundeca-4,9-diynyl)-1-hydroxy-4-methoxynaphthalene, bis-(valine ester) (11.6 mg) is taken up in diethyl ether (1 ml) and treated with 10 drops of a saturated hydrogen chloride-ether mixture (prepared by bubbling anhydrous hydrogen chloride gas into anhydrous ether). A white precipitate immediately forms. The ether is evaporated and the above process repeated. After evaporation of the ether a second time the solid is covered with ether and the mixture placed in a sonicator for several minutes. Evaporation of the ether gives 13.7 mg of a yellow-white solid. The solid is placed under high vacuum (0.05 mm) overnight to provide 12.7 mg of the title compound as a yellow-white solid, mp 127°–130° C. The solid is very hydroscopic, becoming a sticky paste upon exposure to air over a period of 5–10 minutes.

Anal. Found: C, 61.47; H, 7.15; N, 4.36.

EXAMPLE 6

2(11-Hydroxyundeca-4,9-diynyl)-1-hydroxy-4-methoxynaphthalene, bis (succinate) (Refer to Chart B, B-1 to B-2a)

A flame dried 50 ml 2-necked round bottom flask, equipped with a magnetic stir bar and nitrogen inlet tube is charged with 2(11-hydroxyundeca-4,9-diynyl)-1-hydroxy-4-methoxynaphthalene (0.695 g), 4-dimethylaminopyridine (37.2 mg), pyridine (25 ml), and succinic anhydride (1.18 g), and stirred at room temperature 26 hours. The pH of the mixture is adjusted to three using 2M sodium hydrogensulfate (150 ml). The products are extracted three times with ethyl acetate and the combined organic extracts washed with brine, dried with magnesium sulfate, filtered, and concentrated to provide 1.64 g of an orange-brown slurry.

The above material is chromatographed on 250 g of CC-4 silica gel eluting with 30% acetone/hexane. An initial fraction of 400 ml is collected followed by 10 ml fractions to fraction 125, 15 ml fractions until fraction 175, and 20 ml fractions thereafter. Fractions 64–196 are homogeneous by TLC and are combined and concentrated to give 0.95 g of a pink solid, mp 95°–100° C. The solid is recrystallized in a hexane/ethyl acetate (3:2) mixture. Drying of the solid at room temperature under low vacuum (0.05 mm) gives 0.76 g of the title compound as a white-pink solid, mp 109°–111° C.

NMR (CDCl$_3$; TMS): $\delta$ 10.3–10.1; 8.35–8.15; 7.85–7.4; 6.7; 4.8–4.65; 4.0; 3.2–2.6; 2.5–1.55.

Infrared (Nujol): $\nu_{max}$ 1745, 1715, 1419, 1402, 1365, 1326, 1272, 1254, 1230, 1219, 1208, 1186, 1158, 1120, 955, 764, and 630 cm$^{-1}$.

Ultraviolet: $\lambda_{max}$ (ethanol) 213, 238, 290, 299, 310, 326.

Anal. Found: C, 67.14; H, 6.01.

TLC (Silica Gel GF): R$_f$=0.16 in 30% acetone/hexane.

EXAMPLE 7

2-(11-Hydroxyundeca-4,9-diynyl)-1-hydroxy-4-methoxynaphthalene, bis (succinate, potassium salt)
(Refer to Chart B, B-2a to B-2b)

The starting material, 2-(11-hydroxyundeca-4,9-diynyl)-1-hydroxy-4-methoxynaphthalene, bis (succinate) (31.8 mg) is dissolved in ½ ml of methanol. A solution containing potassium carbonate (15.8 mg) in water is added and the entire contents stirred for 10 minutes at room temperature. The methanol-water is evaporated under reduced pressure and the remaining residue taken up in tetrahydrofuran. The tetrahydrofuran is evaporated under reduced pressure. The addition and evaporation of tetrahydrofuran is repeated five more times to provide the title compound as a light brown solid.

EXAMPLE 8

2-(11-Hydroxyundeca-4,9-diynyl)-1-hydroxy-4-methoxynaphthalene, bis (succinate, THAM salt)
(Refer to Chart B, B-2a to B-2c)

Procedure 1: 2-(11-Hydroxyundeca-4,9-dinyl)-1-hydroxy-4-methoxynaphthalene, bis (succinate) (30.3 mg) is taken up in 0.5 ml of methanol. A solution containing tris-(hydroxymethyl)aminomethane (13.4 mg) in 1.8 ml of methanol (with several drops of water) is added. The mixture is heated to 65° C. for 10 minutes. After cooling the methanol is evaporated under reduced pressure. To assist in solid formation, methylene chloride is added and then evaporated. The resulting product is an amorphous solid.

EXAMPLE 9

2-(11-Hydroxyundeca-4,9-diynyl)-1,4-naphthoquinone
(Refer to Chart C, C-1 to C-2)

2-(11-Hydroxyundeca-4,9-diynyl)-1-hydroxy-4-methoxynaphthalene (0.229 g) is dissolved in 2 ml of acetonitrile and 1.5 ml of water and placed in an ice bath. Addition of ceric ammonium nitrate (1.12 g) in 3 ml of cold 50% acetonitrile/water is carried out over a 15 minute period to the above solution. Stirring is continued an additional 30 minutes with cooling in an ice bath. The entire mixture is poured into a separatory funnel and additional water is added. The desired material is extracted three times with methylene chloride. The combined organic extracts are washed with water, saturated sodium bicarbonate solution, and brine, dried with magnesium sulfate, filtered, and concentrated to give 0.215 g of a yellow oil.

The oil is chromatographed on 20 g of HPLC grade silica gel eluting with 20% acetone/hexane. The fractions corresponding to the desired product are not homogeneous by TLC. An additional chromatography is carried out on 20 g of HPLC grade silica gel eluting with 2% acetone/methylene chloride. Again, the fractions containing the desired compound are not homogeneous by TLC (impurity of lower $R_f$). Decomposition on silica gel is shown by spotting the sample on a TLC plate in 15 minute intervals and observing that the material remaining on the plate longest shows the greatest amount of decomposition. As a result, no further purification is attempted. Solvent evaporation gives 0.168 g of the title compound as a light brown oil.

NMR (CDCl$_3$; TMS): δ 8.2–7.95; 7.9–7.65; 6.85; 4.25; 3.15–2.85; 2.8–2.5; 2.45–1.4.

Infrared (neat): $\nu_{max}$ 3446, 3319, 2936, 2908, 2866, 1663, 1620, 1595, 1453, 1433, 1418, 1367, 1329, 1304, 1259, 1237, 1231, 1142, 1016, 973, 950, 782, 728, 708, 673, and 661 cm$^{-1}$.

Ultraviolet: $\lambda_{max}$ (ethanol) 246, 252, 260, 265, 333.

Mass Spectrum: m/e Found: 320.1397.

Anal. Found: C, 78.12; H, 6.29.

EXAMPLE 10

2-(12-Hydroxydodeca-5,10-diynyl)-1,4-naphthoquinone (Refer to Chart C, C-1 to C-2)

2-(12-Hydroxydodeca-5,10-diynyl)-1-hydroxy-4-methoxynaphthalene (80 mg) is dissolved in 1 ml of acetonitrile and 0.75 ml of water. This mixture is cooled in an ice bath and the addition of ceric ammonium nitrate (0.377 g) in 2 ml of 50% acetonitrile/water is carried out over 10 minutes. Stirring is continued an additional 30 minutes (after only 5 minutes a yellow precipitate forms). The above contents are poured into a separatory funnel and additional water is added. The mixture is extracted three times with methylene chloride and the combined organic extracts are washed with water, saturated sodium bicarbonate, and brine, dried with magnesium sulfate, filtered, and concentrated to provide 74.9 mg of the title compound as a yellow solid, mp 88°–89.5° C. By TLC (in 2% acetone/methylene chloride) the material is fairly clean, with a small amount of impurities at lower $R_f$. Drying the sample under low vacuum (0.2 mm) overnight changes the melting point slightly, mp 89°–90.5° C.

NMR (CDCl$_3$; TMS): δ 8.25–8.0; 7.9–7.7; 6.85; 4.25; 2.65–2.45; 2.45–1.4.

Infrared (Nujol): $\nu_{max}$ 3486, 1663, 1619, 1590, 1328, 1300, 1292, 1273, 1022, 1013, 959, 921, 791, 784, 738, 708, and 622 cm$^{-1}$.

Ultraviolet: $\lambda_{max}$ (ethanol) 210, 226, 246, 251, 260, 265, 332.

Mass Spectrum: m/e Found: 334.1557.

TLC (Silica Gel CF): $R_f$=0.25 in 2% acetone/methylene chloride.

FORMULAS

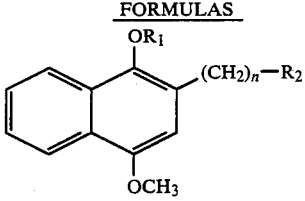

I

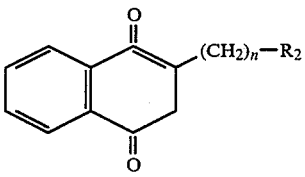

II

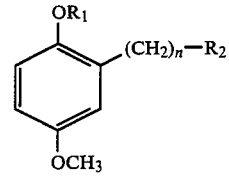

III

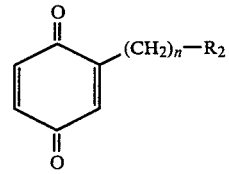

IV

CHART A
SCHEME 1

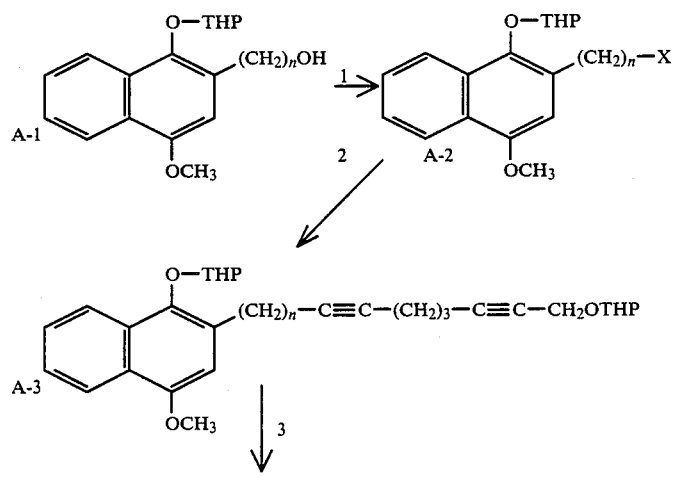

CHART A
SCHEME 1
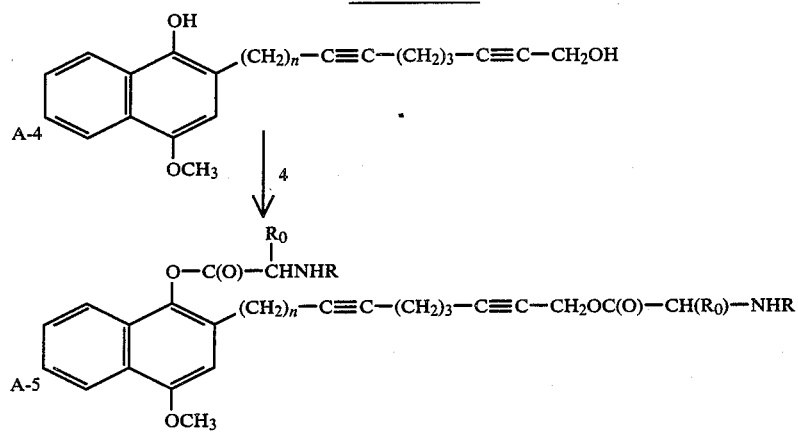
Eg: $R_0$ = isopropyl
A-5a - R = t-butyloxycarbonyl
A-5b - R = H
A-5c - R = hydrochloride salt
CHART B
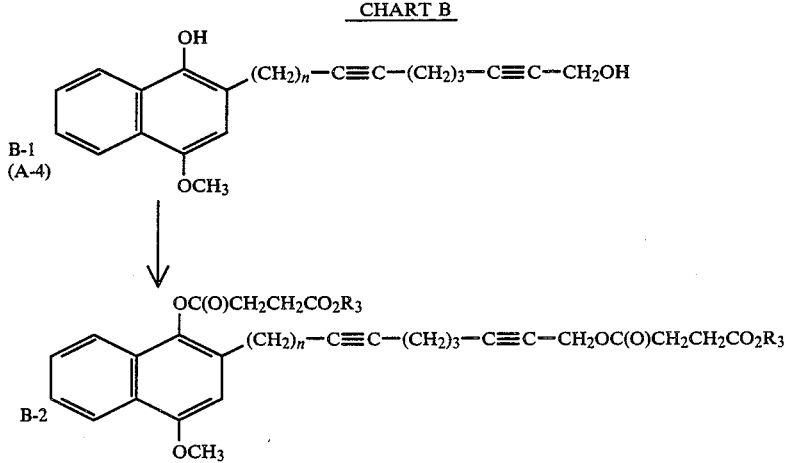
B-2a - R = H
B-2b - R = potassium
B-2c - R = tris-(hydroxymethyl)aminomethyl (THAM)
CHART C
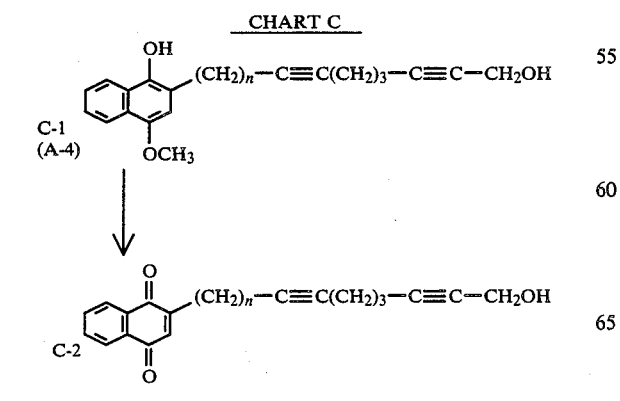
CHART D
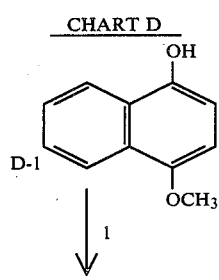

-continued
CHART D
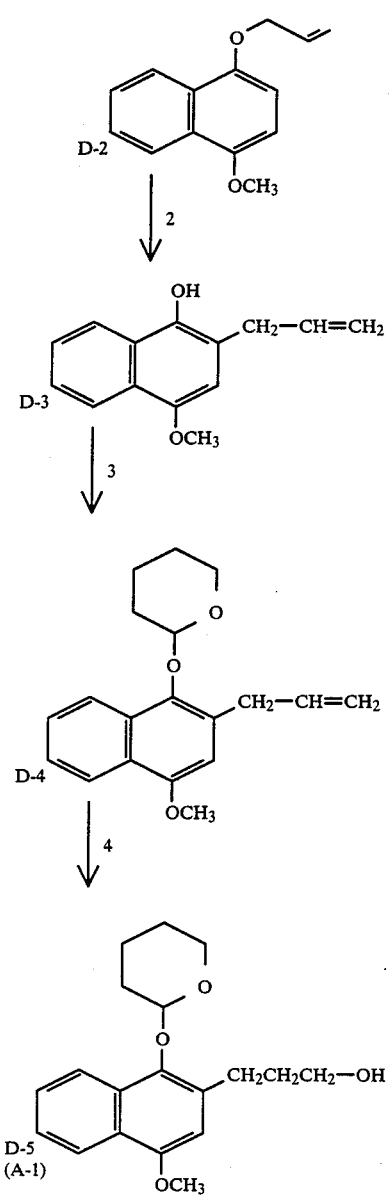
CHART E
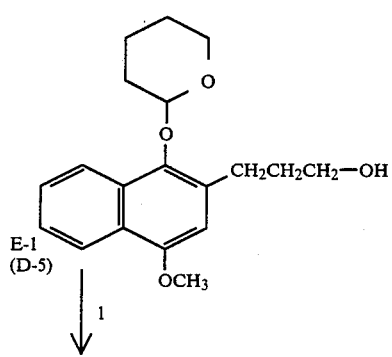
-continued
CHART E
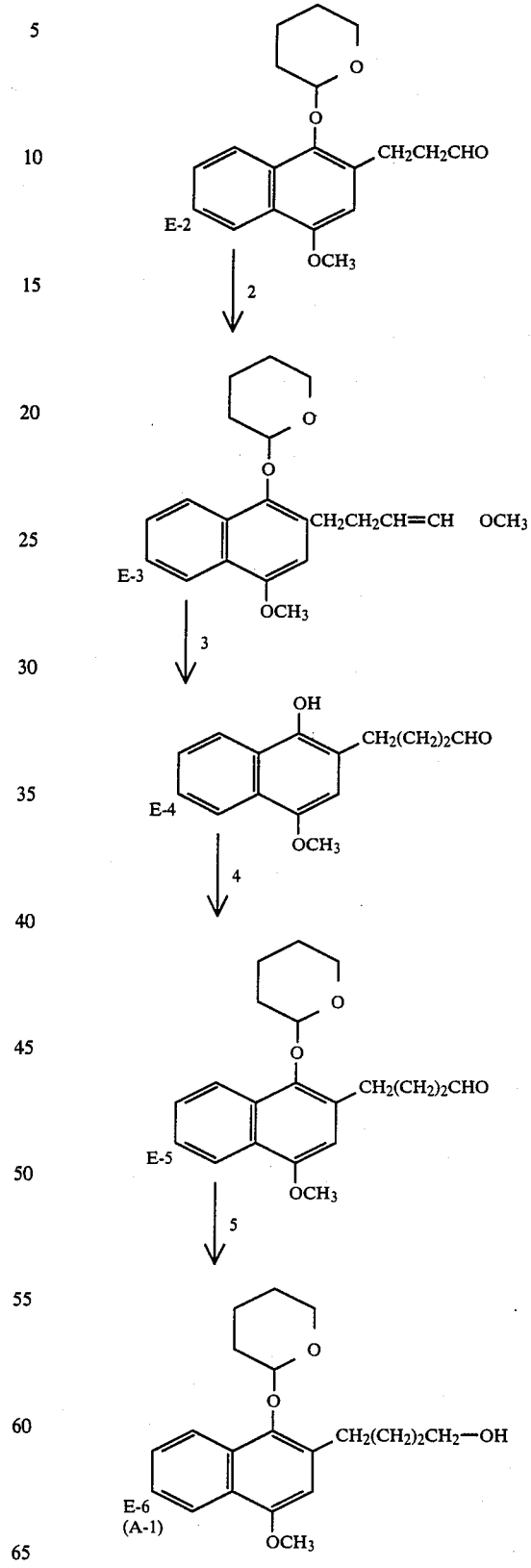
We claim:
1. A compound having the formula

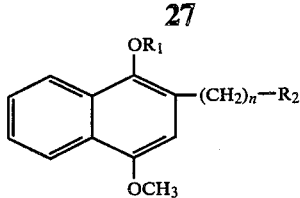
wherein $R_1$ is hydrogen; $R_2$ is $-C\equiv C-(CH_2)_m-C\equiv C-(CH_2)_p-OR_1$ and n is 3 or 4, m is 1 to 5, inclusive and p is 0 to 3 inclusive.
2. A compound of claim 1, 2-(11-hydroxyundeca-4,9-diynyl)-1-hydroxy-4-methoxynaphthalene.
3. A compound of claim 1, 2-(12-hydroxydodeca-5,10-diynyl)-1-hydroxy-4-methoxynaphthalene.
* * * * *